United States Patent [19]

Kelsey et al.

[11] Patent Number: 5,306,493
[45] Date of Patent: Apr. 26, 1994

[54] FELV-INFECTED FELINE CELL LINE

[75] Inventors: William H. Kelsey, Alameda; Edmund P. Bass, Menlo Park, both of Calif.

[73] Assignee: Miles Inc., Pittsburgh, Pa.

[21] Appl. No.: 437,551

[22] Filed: Nov. 15, 1989

Related U.S. Application Data

[63] Continuation of Ser. No. 915,088, Oct. 3, 1986, abandoned.

[51] Int. Cl.$^5$ .................. A61K 39/12; C12N 5/06; C12P 21/00
[52] U.S. Cl. ............................ 424/89; 514/2; 514/8; 530/403; 435/70.1; 435/5; 435/240.2; 435/240.1
[58] Field of Search ............ 424/89; 514/8, 2; 530/403; 435/70.1, 5, 240.2, 240.1

[56] References Cited

U.S. PATENT DOCUMENTS

| | | | |
|---|---|---|---|
| 3,966,907 | 6/1976 | Jarrett et al. | 424/89 |
| 4,034,081 | 7/1977 | Jarrett et al. | 424/89 |
| 4,086,134 | 4/1978 | Jarrett et al. | 424/89 |
| 4,117,112 | 9/1978 | Jarrett et al. | 424/89 |
| 4,264,587 | 4/1981 | Pedersen et al. | 424/89 |
| 4,332,793 | 6/1982 | Olson | 424/89 |
| 4,699,785 | 10/1987 | Pedersen | 424/89 |
| 4,772,466 | 9/1988 | Allison et al. | 424/89 |

FOREIGN PATENT DOCUMENTS 64417 9/1973 Belgium.

OTHER PUBLICATIONS

Crandell et al., In Vitro, vol. 9, No. 3, (1973), pp. 176-185.
Park et al., Misaengmul Hakhoe Chi, (1983), vol. 21(2), pp. 61-70, [Chem. Abs. vol. 99 No. 136704j].
Sarma & Log, Virology (1973) 54:160-169.
Russell & Jarrett, Int'l J. Cancer (1978) 21:768-778.
Jarrett (1980), Feline Leukemia Virus—Developments in Cancer Research vol. 4, pp. 473-479.
Jarrett & Russell, Int'l Cancer, 1978 21:466-472.
Sarma et al., J. Nat'l Cancer Inst. (1978) 60:871-874.
Schaller & Olsen, Infect. Immun. (1975) 12:1405-1510.

Primary Examiner—Merrell C. Cashion, Jr.
Assistant Examiner—T. D. Wessendorf
Attorney, Agent, or Firm—Joseph C. Gil; Lyndanne M. Whalen

[57] ABSTRACT

Crandell feline kidney cells infected with a Rickard isolate of FeLV, i.e., FeLV-$A_{R1}$, are provided, the infected cells being capable of producing viral materials in amounts sufficient for formulating FeLV vaccines. Processes for producing viral material and FeLV vaccines utilizing the viral material thus prepared also are provided.

7 Claims, No Drawings

FELV-INFECTED FELINE CELL LINE

This application is a continuation of application Ser. No. 06/915,088 filed Oct. 3, 1986, now abandoned.

TECHNICAL FIELD

The present invention relates to viral antigens and vaccines and in particular to feline cell lines infected with feline leukemia virus (FeLV) which are capable of producing both feline leukemia virus and viral glycoprotein antigen.

BACKGROUND OF THE INVENTION

Feline leukemia virus (FeLV) is a retrovirus consisting of three subgroups designated A, B, and C. The FeLV subgroups were identified initially by viral interference and cross-neutralization. Sarma & Log, *Virology* (1973) 54:160-169; see also, Russell & Jarrett, *Int'l J. Cancer* (1978) 21:768-778; and Jarrett (1980) in *Feline Leukemia Virus—Developments in Cancer Research Vol. 4*, Hardy et al., eds., Elsevier North Holland, Inc., pp. 473-479. Feline leukemia virus is discussed also in Jarrett & Russell, *Int'l J. Cancer* (1978) 21:466-472; Sarma et al., *J. Nat'l Cancer Inst.* (1978) 60:871-874; and Schaller & Olsen *Infect. Immun.* (1975) 12:1405-1510.

FeLV is infectious in cats. It is responsible for a number of diseases, including lymphoplastic or aplastic anemia, myelosuppression, thymic atrophy, and thrombocytopenia, as well as reproductive failure, e.g., abortion, fetal resorption, and stillbirths. Neoplastic manifestations of FeLV infection, such as lymphosarcoma, account for only a small portion of the morbidity and mortality caused by FeLV. FeLV infection in cats, however, also causes suppression of the immune system, thereby exposing the animal to opportunistic infections by a variety of microorganisms.

Vaccines have been developed for FeLV. See, e.g., U.S. Pat. No. 4,332,793 to Olson, U.S. Pat. No. 4,264,587 to Pedersen et al., U.S. Pat. No. 4,117,112 to Jarrett et al., U.S. Pat. No. 4,086,134 to Jarrett et al., U.S. Pat. No. 4,034,081 to Jarrett et al., U.S. Pat. No. 3,966,907 to Jarrett et al., and Belgian Patent Application R 64 417 DG to the University of Glasgow.

In particular, a FeLV vaccine may be prepared from inactivated FeLV virus and from envelope glycoprotein (gp70), the antigen with which it is thought protective antibody must react. Such viral material generally may be produced by culturing infected feline cell lines, but it has been impossible to predict whether a particular feline cell line will produce viral material of appropriate quality in quantities sufficient to be useful for commercial production of FeLV vaccines. Moreover, a cell line which satisfactorily produces viral material for a given strain of FeLV may not produce adequate protection against other strains or may produce viral material that for other reasons is ineffective in vaccine formulations.

Thus, there is a continuing need to develop new systems for producing FeLV viral material that can be used in formulating commercially useful FeLV vaccines. It should also be noted that FeLV viral material is useful in the preparation of diagnositic reagents, and thus, new cell lines for its production are needed for that purpose as well.

SUMMARY OF THE INVENTION

This invention provides for Crandell Feline Kidney (CRFK) cells infected with a Rickard isolate of FeLV, i.e., FeLV-$A_{R1}$, the infected cells being capable of producing FeLV virus in amounts sufficient for formulating FeLV vaccines.

This invention also provides for a process for producing FeLV viral material, which process comprises infecting CRFK cells with an FeLV virus, such as FeLV-$A_{R1}$, cultivating the infected CRFK cells, and recovering the viral material. The invention further provides for a FeLV vaccine prepared from the viral material thus prepared.

Surprisingly, it has now been found that the FeLV-infected Crandell cell line of the subject invention stably yields high titers of FeLV which can be used in efficacious FeLV vaccines. Particularly, it produces 10 to 100 times higher titers of gp70 than do normal feline embryo cells.

DETAILED DESCRIPTION OF THE INVENTION

The feline cell line employed in the present invention is the Crandell Feline Kidney (CRFK) line obtained from the American Type Culture Collection (ATCC CCL94). CRFK cells are described in Crandell et al., *In Vitro* (1973) 9:176-185.

The CRFK cell line is infected with a Rickard isolate of FeLV, i.e., FeLV-$A_{R1}$. Upon culturing, the infected cell line, designated ACFL, becomes chronically infected and produces viral material at a rate of at least $10^3$ to $10^7$ focus-forming units per milliliter. The FeLV virus produced by the cells exhibits a titer of $10^5$, preferably $10^6$, focus-forming units per milliliter (FFU/ml) in one to three weeks, and at least $2 \times 10^6$, preferably $3 \times 10^6$, FFU/ml thereafter.

On the other hand, when infected with another Rickard isolate, FeLV-$A_{R2}$, the CRFK cells produced less viral material, and the viral material produced was less effective in vaccine formulations. Similarly, viral material produced from another FeLV-$A_{R1}$-infected cell line, AK-D cells, which satisfactorily produce viral material when infected with the Sarma strain of FeLV, was inadequate for formulating vaccines.

The viral material produced by the ACFL cell line may be used in a variety of vaccine formulations within the scope of this invention. The viral material is virulent for cats and must be inactivated before it is used to prepare vaccines.

The viral material may be inactivated by conventional means which maintain immunogenicity. Means of inactivation are known in the art. Particular means of inactivation which have found use herein include heat, formalin, binary ethyleneimine (BEI), ozone, and psoralen. See U.S. Pat. Nos. 4,332,793; 4,264,587; 4,117,112; 4,034,081; and 3,996,907. Preferably, psoralen inactivation will be employed. In this method the live virus is combined in an appropriate medium with the psoralen. The amount of psoralen should be sufficient to provide for a substantially complete inactivation of the virus upon irradiation with long wave ultraviolet radiation. See U.S. Pat. No. 4,545,987.

The vaccine may include an immunologic adjuvant a physiologically-acceptable carrier, for example, an inert carrier such as deionized water, phosphate-buffered saline, saline, or the like. The carrier may also include a physiologically-acceptable adjuvant, such as a mineral oil, vegetable oil, mineral salt, or an immunopotentiator, such as muramyl dipeptide. Such carriers and adjuvants are well known in the art.

Typically, the concentration of the virus in the vaccine formulation, either separated from or within the infected cell, will be from about $10^2$ to about $10^9$ FFU/ml. If needed, the virus may be conveniently concentrated using commercially available equipment. The total dosage generally is at least about $10^2$ FFU per dose, more commonly at least about $10^5$ FFU per dose. It generally will not exceed about $10^9$ FFU per dose.

Usually, a specific dosage at a specific site will be administered in a volume in the range from about 0.1 ml to 4 ml, where the total volume administered will range from 0.5 ml to 8 ml. The number of injections and their temporal spacing may be varied, but one to three injections at one to three week intervals are usually effective.

The vaccine may be administered subcutaneously, intramuscularly, or intraperitoneally. Conveniently, the prepared vaccines will be packaged in small vials holding sufficient vaccine for one dose and having a septum for inserting a hypodermic needle.

The subject invention is further described by reference to the following examples. These examples are not intended to limit the scope of the invention; rather, they are presented merely to facilitate the practice of the invention by those of ordinary skill in the art.

EXAMPLE 1

The production of FeLV virus and gp70 was compared in (1) FeLV-$A_{R1}$ infected CRFK cells, (2) FeLV-$A_{R2}$ infected CRFK cells, and (3) FeLV-$A_{R1}$ infected AK-D cells as follows:

Infection and Culturing

CRFK cells (ATCC CCL94) were seeded at a density of approximately $5 \times 10^6$ cells into a 75 cm$^2$ tissue culture flask in 12 ml of MEN$_{95}$F$'_5$ growth medium and incubated overnight at 37° C. (MEN$_{95}$F$'_5$ is Eagle's Minimum Essential Medium with Earle's salts and nonessential amino acids supplemented with 5% heat-inactivated fetal bovine serum). At 20 hours post-seeding the growth medium was removed from the cell monolayer, and 2 ml of overlay medium (MEN containing 25 $\mu$g/ml of DEAE-Dextran) was added. The cells then were incubated for 1 hour at 37° C. After incubation, the overlay medium was removed, and the cell monolayer was rinsed two times with 10 ml of MEN$_{95}$F$'_5$.

The cell monolayer then was overlayed with 2 ml of FeLV-$A_{R1}$ having titer of approximately $2.5 \times 10^4$ FFU/ml. The virus was allowed to adsorb for 2 hours at 37° C. The multiplicity of infection (MOI) was 0.01. Following the 2 hour adsorption period, cells were fed with 12 ml MEN$_{95}$F$'_5$ growth medium and incubated at 37° C. The initial flask of CRFK cells infected with FeLV-$A_{R1}$ was designated O-ACFL.

Following the initial infection, the medium was changed at three-day intervals. Confluency generally was reached on the seventh day following initial infection, i.e., day seven post-infection (p.i.), at which time the cells were subcultured at a split ratio of 1:10 in a new flask. This same process was carried out at seven-day intervals for 5 weeks, the subsequent flasks being designated 1-ACFL, 2-ACFL, etc.

The same procedure described above for FeLV-$A_{R1}$ infected CRFK cells also was used to infect CRFK cells with FeLV-$A_{R2}$ and to infect AK-D cells with FeLV-$A_{R1}$.

At 7-day intervals p.i., samples of medium containing FeLV-A were withdrawn. The samples were titrated and assayed for p27 as described below with the results shown in Table 1 below, thereby confirming that the cell lines were chronically infected.

Recovery of Viral Material

At confluency, 250 ml MEN$_{95}$F$'_5$ were added to each of 10 roller bottles of fifth passge ACFL cells (5-ACFL). After 72 hours the supernatant was harvested, pooled, and frozen with 10% DMSO and stored at $-85°$ C. Fresh medium was added to the roller bottles and at 144 hours the supernatant was again harvested, pooled, and frozen. The harvests were thawed, pooled, and concentrated 10-fold to a final volume of 500 ml using a Millipore Corporation Pellicon ultrafiltration cassette (100,000 MW exclusion).

The same procedure was used to concentrate virus harvested from fifth passage, FeLV-$A_{R2}$ infected CRFK cells (5-CRFK). The viral material produced by the FeLV-$A_{R1}$ infected AK-D cells was not recovered because the production levels of viral material were too low to be of interest for formulating vaccines.

The pooled and concentrated viral materials from the 5-ACFL and 5-CRFK cell lines were titrated and assayed for p27 as described below. They were also assayed for gp70 and tested for reverse transcriptase activity, again as described below.

Virus Titration: Determination of Focus Forming Units

Standard test cells (clone 81) were plated into 6-cm plastic petri dishes at $2 \times 10^5$ cells/dish in growth medium (McCoy's 5A+15% heat-inactivated fetal calf serum) and incubated in a humidified CO$_2$ incubator. Approximately 20 hours later the medium was withdrawn and 1 ml of DEAE-Dextran (DEAE-D) (25 $\mu$g/ml) in growth medium was added to each dish. The cells were then incubated at 37° C. After 30 minutes the DEAE-D medium was withdrawn, and each dish was washed once with 2 ml of growth medium.

Virus inocula of 0.2 to 1.0 ml per dish were applied, the dishes were incubated, with occasional shaking, for 30 minutes at 37° C., and then 5 ml of growth medium was added to each dish. On day 3 p.i., 3 ml of growth medium was added. On day 7 p.i., all growth medium was removed and replaced with 5 ml of fresh growth medium. On day 10 p.i., 3 ml of fresh growth medium was added.

Foci were read on day 12 p.i. The foci typically are 0.5 to 2 mm in diameter and consist of piled, small, dark, round cells on a dense monolayer. Generally, no retraction of the monolayer occurs in the focus area.

Further details of this procedure are set forth in Fischinger et al., *J. Virol* (1974) 14:177–179.

p27 Assay

Supernatants from infected cultures were assayed for FeLV group specific (p27) antigen by an ELISA (Leukassay*F, commercially available from Pitman Moore) according to the manufacturer's specified procedure.

gp70 Assay

Supernatants from infected cultures were assayed for FeLV gp70 by an indirect ELISA. A microtiter plate coated with polyclonal goat anti-FeLV gp70 antibody (NCI Repository) was used as the capturing solid phase. The antibody used to detect virus bound to the plate was a mouse anti-FeLV gp70 monoclonal antibody (AGRI). The second antibody was a peroxidase-conjugated goat anti-mouse immunoglobulin (Boehringer Mannheim Biochemicals). The substrate used was tetramethylbenzidine in citrate buffer.

Quantitation of gp70 was based on comparison with a standard sample of purified virus. The standard virus sample was prepared by banding virions in a preformed linear 15-60% sucrose gradient by velocity sedimentation in an ultracentrifuge using standard methods. Test and standard samples were diluted serially and assayed by ELISA. The optical density of each dilution point was determined. The titer of the test sample relative to the virus standard was computed at 50% of the maximum optical density of the test sample.

Reverse Transcriptase Assay

Cell culture supernatants were tested for reverse transcriptase activity by the following procedure: Fifty microliters of 2× cocktail were added to each 50 μl aliquot of cell culture supernatant. (2× Cocktail contains 80 mM Tris-HCl (pH 8.2), 120 mM KCl, 1.2 mM MnAcetate, 1 $OD_{260}$ poly-A, 0.01 $OD_{260}$ oligo-$dT_{12-18}$ 0.1 mM TTP, 0.4% NP-40, 3.0 mM dithiothreitol, 0.1 μCi/μl $^3$H-TTP in deionized water). The mixture was incubated for 30 minutes at 37° C., whereupon the reaction was stopped, and the DNA was precipitated by adding 0.2 ml of 0.1M sodium polyphosphate and 0.3 ml of 20% cold trichloroacetic acid (TCA) to each tube. The tubes then were incubated for 30 minutes at 0° C. Samples were collected on 2.4 cm Whatman GF/A filters. Sample tubes were washed twice with cold 5% TCA. Filters were washed twice with cold 5% TCA followed by cold 100% ethanol and then dried. The radioactivity of the viral-specific DNA was counted in 7 ml scintillation fluid in a Beckman Instruments model LS-1800 scintillation counter.

Results

The titration and various assay results are reported in Table 1. As shown therein, the ACFL line produced virus of higher titer, sooner after infection, and continued to produce virus and viral antigen at a higher sustained level than did CRFK cells infected with FeLV-$A_{R2}$ or AK-D cells infected with FeLV-$A_{R1}$. The infected AK-D cells did not produce virus of sufficiently high titer to be useful in vaccine production. This result was unexpected, because AK-D cells have been used successfully to produce quantities of the Sarma strain of FeLV-A sufficient for preparing experimental vaccines.

TABLE 1

Titration and Assay Data From Cell Lines Infected With FeLV-$A_R$

| System | Passage | Weak P.I. | Titer FFU/ml | Dil. | p27 ELISA Plate | p27 ELISA O.D. | gp70 ELISA | RT activity cpm/50 μl |
|---|---|---|---|---|---|---|---|---|
| ACFL | 0-ACFL | 1 | ND | Neat | + | 1.385* | ND | ND |
| | 1-ACFL | 2 | ND | Neat | + | 2.37 | ND | ND |
| | 2-ACFL | 3 | $1.15 \times 10^6$ | Neat | + | 2.96 | ND | ND |
| | 3-ACFL | 4 | $2.25 \times 10^6$ | Neat | + | 3.10 | ND | ND |
| | 4-ACFL | 5 | $3.75 \times 10^6$ | Neat | + | 2.87 | ND | ND |
| | 5-ACFL | 6 | | | | | | |
| | 5L Pool | | $1.73 \times 10^6$ | Neat | + | 3.26 | 1:95** | ND |
| | 10X Conc. | | $2.18 \times 10^7$ | Neat | + | 3.20 | 1:16 | 108,590 |
| | | | | 1:10 | + | 2.10 | ND | ND |
| CRFK-FeLV-$A_{R2}$ | 0-CRFK | 1 | ND | Neat | + | 1.997 | ND | ND |
| | 1-CRFK | 2 | ND | Neat | + | 2.92 | ND | ND |
| | 2-CRFK | 3 | $3.20 \times 10^5$ | Neat | + | 3.01 | ND | ND |
| | 3-CRFK | 4 | $3.75 \times 10^5$ | Neat | + | 3.08 | ND | ND |
| | 4-CRFK | 5 | $5.25 \times 10^5$ | Neat | + | 2.69 | ND | ND |
| | 5-CRFK | 6 | | | | | | |
| | 5L Pool | | $4.90 \times 10^5$ | Neat | + | 3.25 | 1:112** | ND |
| | 10X Conc. | | $4.89 \times 10^6$ | Neat | + | 3.29 | 1:20 | 61,200 |
| | | | | 1:10 | + | 1.814 | ND | ND |
| AKD-FeLV-$A_{R1}$ | 0-AK-D | 1 | ND | Neat | + | 0.421 | ND | ND |
| | 1-AK-D | 2 | ND | Neat | + | 0.996 | ND | ND |
| | 2-AK-D | 3 | $3.20 \times 10^4$ | Neat | + | 1.597 | ND | ND |
| | 3-AK-D | 4 | $1.85 \times 10^4$ | Neat | + | 0.994 | ND | ND |
| | 4-AK-D | 5 | $7.75 \times 10^3$ | Neat | + | 0.980 | ND | ND |

*Positive control = 3.04; Negative control = 0.09
**Equivalent dilution of virus standard as determined by graphic interpolation.
ND = Not Done

EXAMPLE 2

The production of FeLV-$A_{R1}$ viral material in eighth-passage, chronically infected ACFL cells and in eleventh-passage, chronically infected normal feline embryo cells was compared. Infection, culturing, titration, and assaying were performed as described above in Example 1. The results are reported below in Table 2. As shown therein, the ACFL line produced more virus and gp70 viral antigen than did the normal feline embryo cells infected with the same virus isolate.

TABLE 2

Titration and Assay Data From ACFL and Normal Feline Embryo Cells Infected With FeLV-$A_{R1}$

| System | Titer FFU/ml | Dil. | p27 ELISA Plate | p27 ELISA O.D.* | gp70 ELISA ARB** | RT activity cpm/50 μl |
|---|---|---|---|---|---|---|
| ACFL | $1.0 \times 10^6$ | Neat | + | 3.26 | 21 | 55,828 |
| | | 1:10 | + | 3.22 | | |
| | | 1:100 | + | 2.46 | | |
| Normal Feline Embryo | $2.14 \times 10^5$ | Neat | + | 1.250 | 2.7 | 11,204 |

*ACFL: Positive control = 3.17; Negative control = 0.088 Feline Embryo: Positive control = 3.01; Negative control = 0.087
**ARB = One ARB unit is an arbitrary measurement equivalent to 1/100 of a standard preparation of purified FeLV-A (Rickard).

EXAMPLE 3

The effectiveness of vaccine formulations derived from the ACFL and FeLV-$A_{R2}$ infected CRFK cell lines was compared as follows:

Vaccine Formulations

A first vaccine formulation was prepared from the pooled, concentrated viral material produced by the ACFL cells of Example 1. The concentrated virus preparation was inactivated by 0.2% formalin for approximately 48 hours at room temperature. The vaccine contained approximately $10^7$ FFU of virus suspension and an oil-in-water adjuvant in a 1:1 ratio.

A second vaccine formulation was prepared in the same manner from the pooled, concentrated virus produced by the FeLV-$A_{R2}$ infected CRFK cells of Example 1. It contained approximately $2.4 \times 10^6$ FFU of virus.

Feline Subjects

Eighteen cats (minimal disease cats, Liberty Labs, Liberty Corner, N.J.), nine males and nine females, 14 to 15 weeks of age, were divided into three groups of six cats each. Groups I and II were vaccinated intramuscularly twice with a 3-week interval with 1 ml, respectively, of the first and second vaccine formulations. Group III cats served as unvaccinated controls. All cats were challenged oronasally two weeks after the second inoculation with $10^6$ FFU of live FeLV-$A_{R1}$.

Blood samples were taken weekly. The samples were assayed for FeLV antigens, by p27 ELISA as described above, and by indirect immunofluorescence, as described below. They also were tested by the virus isolation protocol described below.

Immunofluorescence Assay (IFA)

Smears of blood from vaccinated cats were tested for the presence of FeLV antigens in blood cells by indirect immunofluorescence. The first antibody was goat anti-FeLV p27 (NCI Repository); the second antibody was fluorescein-conjugated rabbit anti-goat IgG (Cooper Biomedical/Cappel Laboratories). Slides were examined on a Zeiss Photomicroscope III equipped for epifluorescence.

Virus Isolation Protocol

The cats were kept in isolation. Blood samples were aseptically collected. Serum was separated by centrifugation and filtered through 0.2 μm filter discs (e.g., Gelman Acrodiscs). Lymphocytes were separated by density centrifugation by diluting 1 to 1.5 ml EDTA-treated blood with 1 to 1.5 ml phosphate buffered saline (PBS), layering the suspension onto 2.5 ml Ficoll-Paque (Pharmacia), and centrifuging the tubes at 800× g for 30 minutes. Cells banded at the interface were harvested and washed once in PBS. Lymphocytes were resuspended in 0.2 ml of autologous serum.

An indicator cell culture was prepared by growing AK-D feline lung cells (ATCC CCL150) in F12K medium supplemented with 15% heat-inactivated fetal bovine serum and antibiotics (100 units/ml Penicillin and 100 μg/ml Streptomycin).

The AK-D cells were harvested by trypsin treatment. Approximately $5 \times 10^5$ cells were seeded into each 25 $cm^2$ flask with 4 ml medium. The cultures were incubated at 37° C. with 5% $CO_2$ for one day. The medium was removed, and the resuspended lymphocytes (0.2 ml) were inoculated onto the AK-D cell monolayer. Control cultures were inoculated with PBS. After the inoculum was absorbed for 1 hour, 5 ml of medium was added. The medium was changed the next day. Thereafter, the cells were cultured at 37° C. with 5% $CO_2$, fed on day 3 or 4, and subcultured on day 7. The cultures were maintained for up to six weeks.

Cell culture supernatant was collected for FeLV p27 antigen assay before feeding (3 to 5 days post-inoculation) and also 3 to 5 days postsubculturing. The collected supernatant then was tested for the presence of FeLV p27 by ELISA (Leukassay*F, Pitman Moore) according to the manufacturer's specified procedure. Cultures that gave two consecutive positive assays were considered "virus isolation positive"; cultures that remained negative for six weeks were considered "virus isolation negative".

The validity of this protocol was confirmed by testing supernatants for the presence of infectious retrovirus using the clone-81 virus assay described above in Example 1.

Results

At eleven weeks post-challenge none of the Group I cats were viremic by IFA or p27 ELISA assays. In contrast 4 of 6 Group II cats and 5 of 6 Group III cats were viremic by both assays. At post-challenge week five, 5 of 6 cats in Group II and 6 of 6 cats in Group III were virus isolation positive whereas 0 of 6 cats in Group I were virus isolation positive.

Virus was not isolated from the blood of the two cats that were positive by ELISA the day before challenge. Since virus isolation is generally a more sensitive test than ELISA, the ELISA results are considered to be spurious. It also is not known whether the failure of the vaccine produced from FeLV-$A_{R2}$ grown in CRFK cells may be attributed to the effective dose, the characteristics of the antigen(s), and/or other factors.

In summary, the chronically infected ACFL line produced more virus and gp70 viral antigen than did the other cell line-virus isolate combinations studied. Virus from ACFL produced an efficacious vaccine, while virus from CRFK cells infected with a different isolate did not yield an efficacious vaccine. The ACFL line constitutes an improved system for producing high titer FeLV virus and the virus produced is useful in formulating vaccines. The ACFL virus also would be useful for production of diagnostic reagents.

These results are summarized below in Table 3.

TABLE 3

| | | Summary of Serum FeLV ELISA, IFA, and Virus Isolation Data From Cats Vaccinated With Inactivated FeLV Vaccines | | | | | | | | | | | | |
|---|---|---|---|---|---|---|---|---|---|---|---|---|---|---|
| Group | Test | D -15 | D 21 | D 34 | D 49 | D 55 | D 64 | D 70 | D 77 | D 84 | D 91 | D 98 | D 105 | D 112 |
| I | Serum ELISA | 0/6 | 0/6 | 1/6 | 0/6 | 0/6 | 0/6 | 0/6 | 1/6 | 0/6 | 0/6 | 0/6 | 0/6 | 0/6 |
| | IFA | | 0/6 | 0/6 | 0/6 | 0/6 | 0/6 | 0/6 | 0/6 | 0/6 | 0/6 | 0/6 | 0/6 | 0/6 |
| | Virus Isol. | | | 0/1 | | | | 0/6 | | | | 0/6* | | |
| II | Serum ELISA | 0/6 | 0/6 | 1/6 | 0/6 | 4/6 | 4/6 | 5/6 | 5/6 | 5/6 | 4/6 | 4/6 | 4/6 | 4/6 |
| | IFA | | 0/6 | 0/6 | 0/6 | 1/5 | 4/6 | 4/6 | 5/6 | 5/6 | 4/6 | 4/6 | 5/6 | 4/6 |
| | Virus | | | 0/2 | | | | 5/6 | | | | | | |

TABLE 3-continued

Summary of Serum FeLV ELISA, IFA, and Virus Isolation Data From Cats Vaccinated With Inactivated FeLV Vaccines

| Group | Test | D -15 | D 21 | D 34 | D 49 | D 55 | D 64 | D 70 | D 77 | D 84 | D 91 | D 98 | D 105 | D 112 |
|---|---|---|---|---|---|---|---|---|---|---|---|---|---|---|
| III | Isol. Serum ELISA | 0/6 | 0/6 | 0/6 | 0/6 | 3/6 | 5/6 | 5/6 | 5/6 | 5/6 | 5/6 | 5/6 | 5/6 | 5/6 |
|  | IFA |  | 0/6 | 0/6 | 0/6 | 3/6 | 4/6 | 5/6 | 5/6 | 5/6 | 5/6 | 5/6 | 6/6 | 5/6 |
|  | Virus Isol. |  |  |  |  |  |  | 6/6 |  |  |  |  |  |  |
|  |  | Baseline |  |  |  |  |  |  |  |  |  |  |  |  |

Groups I and II Vaccinated: Day 0 and Day 21
Groups I, II & III Challenged: Day 35
Data reported as number of positive per group
* = assay in progress
D = day All publications cited in this application are indicative of the level of skill of those skilled in the art to which this invention pertains. Each publication is individually incorporated herein by reference in the same location and to the same extent as if each publication had been individually incorporated by reference.

The invention now being fully described, it will be recognized by those skilled in the art to which this invention pertains that many modifications and variations can be made to the specific procedures described herein without departing from the spirit or scope of the appended claims.

What is claimed is:

1. Crandell Feline Kidney cells with a Rickard isolate of feline leukemia virus designated FeLV-$A_{R1}$.

2. The cells of claim 1, wherein said cells produce viral material in an amount of at least $10^3$ focus-forming units per milliliter.

3. A process for the production of feline leukemia virus viral material, which process comprises:
   cultivating Crandell Feline Kidney cells chronically infected with a Rickard isolate feline leukemia virus which has been designated FeLV-$A_{R1}$ in a cell culture medium, and
   recovering the viral material from said medium.

4. The process of claim 3, wherein said viral material is the Rickard isolate of feline leukemia virus designated FeLV-$A_{R1}$ or envelope glycoprotein gp70.

5. A feline leukemia virus vaccine comprising:
   inactivated viral material produced by Crandell Feline Kidney cells chronically infected with the Rickard isolate of feline leukemia virus designated FeLV-$A_{R1}$ and a pharmaceutically acceptable carrier or immunologic adjuvant.

6. The feline leukemia virus vaccine of claim 5, wherein said inactivated viral material comprises inactivated Rickard isolate of feline leukemia virus designated FeLV-$A_{R1}$ or envelope glycoprotein gp70.

7. The feline leukemia virus vaccine of claim 5, wherein said feline leukemia virus vaccine comprises from about $10^2$ to about $10^9$ focus-forming units per milliliter of inactivated feline leukemia virus.

* * * * *